(12) United States Patent
Bagherinia

(10) Patent No.: US 9,778,021 B2
(45) Date of Patent: Oct. 3, 2017

(54) EVALUATION OF OPTICAL COHERENCE TOMOGRAPHIC DATA PRIOR TO SEGMENTATION

(71) Applicant: Carl Zeiss Meditec, Inc., Dublin, CA (US)

(72) Inventor: Homayoun Bagherinia, Oakland, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 14/466,774

(22) Filed: Aug. 22, 2014

(65) Prior Publication Data

US 2015/0062590 A1 Mar. 5, 2015

Related U.S. Application Data

(60) Provisional application No. 61/871,467, filed on Aug. 29, 2013.

(51) Int. Cl.
| | |
|---|---|
| *G01B 9/02* | (2006.01) |
| *G06T 7/00* | (2017.01) |
| *A61B 3/10* | (2006.01) |
| *G06T 7/10* | (2017.01) |

(52) U.S. Cl.
CPC .......... *G01B 9/02091* (2013.01); *A61B 3/102* (2013.01); *G01B 9/02083* (2013.01); *G01B 9/02089* (2013.01); *G06T 7/0012* (2013.01); *G06T 7/10* (2017.01); *G06T 2207/10081* (2013.01); *G06T 2207/10101* (2013.01); *G06T 2207/30041* (2013.01); *G06T 2207/30168* (2013.01)

(58) Field of Classification Search
CPC ....... H04B 1/707; H04B 7/2628; H04J 13/00; H04J 13/004; G08C 15/12
USPC ........................................................ 356/479
See application file for complete search history.

(56) References Cited

U.S. PATENT DOCUMENTS

| | | | |
|---|---|---|---|
| 7,330,270 B2 | 2/2008 | O'Hara et al. | |
| 7,575,322 B2 | 8/2009 | Somani | |
| 2006/0171503 A1 | 8/2006 | O'Hara et al. | |
| 2008/0100612 A1 | 5/2008 | Dastmalchi et al. | |
| 2008/0278687 A1 | 11/2008 | Somani | |
| 2009/0073387 A1* | 3/2009 | Meyer ...................... | A61B 3/12 351/246 |
| 2012/0075640 A1 | 3/2012 | Sakagawa et al. | |

(Continued)

OTHER PUBLICATIONS

International Search Report & Written Opinion received for PCT Patent Application No. PCT/EP2014/068286, mailed on Oct. 30, 2014, 12 pages.

(Continued)

*Primary Examiner* — Tarifur Chowdhury
*Assistant Examiner* — Md M Rahman
(74) *Attorney, Agent, or Firm* — Morrison & Foerster LLP

(57) ABSTRACT

An efficient method of evaluating the level of contrast of an OCT dataset is presented. The method develops a metric to segregate useful and not-so-useful data in one or more OCT B-scans, in order to reduce spurious subsequent analyses of the data by downstream segmentation algorithms. It is designed to be fast and efficient and is applied to determining autofocus of an OCT instrument real-time and in identifying a real image from its complex conjugate twin.

20 Claims, 11 Drawing Sheets

(56) References Cited

U.S. PATENT DOCUMENTS

| | | | | |
|---|---|---|---|---|
| 2012/0184845 | A1* | 7/2012 | Ishikawa | A61B 3/102 600/425 |
| 2012/0249956 | A1* | 10/2012 | Narasimha-Iyer | A61B 3/102 351/206 |
| 2012/0249961 | A1 | 10/2012 | Muto | |
| 2012/0274897 | A1* | 11/2012 | Narasimha-Iyer | A61B 3/102 351/206 |
| 2013/0279745 | A1* | 10/2013 | Mitsui | G06K 9/4614 382/103 |

OTHER PUBLICATIONS

Ahlers et al., "Automatic Segmentation in Three-Dimensional Analysis of Fibrovascular Pigmentepithelial Detachment Using High-Definition Optical Coherence Tomography", Br. J. Ophthalmol, vol. 92, 2008, pp. 197-203.

Baroni et al., "Towards Quantitative Analysis of Retinal Features in Optical Coherence Tomography", Medical Engineering & Physics, vol. 29, 2007, pp. 432-441.

Boyer et al., "Automatic Recovery of the Optic Nervehead Geometry in Optical Coherence Tomography", IEEE Transactions on Medical Imaging, vol. 25, No. 5, May 2006, pp. 553-570.

Canny, John, "A Computational Approach to Edge Detection", IEEE Transactions on Pattern Analysis and Machine Intelligence, vol. PAMI-8, No. 6, Nov. 1986, pp. 679-698.

Chiu et al., "Automatic Segmentation of Seven Retinal Layers in SDOCT Images Congruent with Expert Manual Segmentation", Optics Express, vol. 18, No. 18, Aug. 30, 2010, pp. 19413-19428.

Debuc, Delia Cabrera, "A Review of Algorithms for Segmentation of Retinal Image Data Using Optical Coherence Tomography", Chapter 2, Image Segmentation, 2011, pp. 15-54.

Farsiu et al., "Fast Detection and Segmentation of Drusen in Retinal Optical Coherence Tomography Images", Proc SPIE, vol. 6844, 2008, pp. 68440D-1-68440D-12.

Fernandez et al., "Automated Detection of Retinal Layer Structures on Optical Coherence Tomography Images", Optics Express, vol. 13, No. 25, Dec. 12, 2005, pp. 10200-10216.

Folio et al., "Variation in Optical Coherence Tomography Signal Quality as an Indicator of Retinal Nerve Fibre Layer Segmentation Error", Br J Ophthalmol. vol. 96, No. 4, 2012, pp. 514-518.

Gotzinger et al., "Retinal Pigment Epithelium Segmentation by Polarization Sensitive Optical Coherence Tomography", Optics Express, vol. 16, No. 21, 2008, pp. 16410-16422.

Herzog et al., "Robust Extraction of the Optic Nerve Head in Optical Coherence Tomography", CVAMIA-MMBIA, LNCS 3117, 2004, pp. 395-407.

Huang et al., "Image Quality Affects Macular and Retinal Nerve Fiber Layer Thickness Measurements on Fourier-Domain Optical Coherence Tomography", Ophthalmic Surgery, Lasers & Imaging, vol. 42, No. 3, 2011, pp. 216-221.

Huang et al., "Optical Coherence Tomography", Science, vol. 254, Nov. 22, 1991, pp. 1178-1181.

Huang et al., "Signal Quality Assessment of Retinal Optical Coherence Tomography Images", Investigative Ophthalmology & Visual Science,, vol. 53, No. 4, Apr. 2012, pp. 2133-2141.

Ishikawa et al., "Macular Segmentation with Optical Coherence Tomography", Investigative Ophthalmology & Visual Science, vol. 46, No. 6, Jun. 2005, pp. 2012-2017.

Kajić et al., "Robust Segmentation of Intraretinal Layers in the Normal Human Fovea Using a Novel Statistical Model Based on Texture and Shape Analysis", Optics Express, vol. 18, No. 14, Jul. 5, 2010, pp. 14730-14744.

Kang et al., "Diagnostic Efficacy of Computer Extracted Image Features in Optical Coherence Tomography of the Precancerous Cervix", Medical Physics, vol. 38, No. 1, Jan. 2011, pp. 107-113.

Kovesi, Peter, "Phase Congruency Detects Corners and Edges", School of Computer Science & Software Engineering, 2003, 10 pages.

Liu et al., "Quality Assessment for Spectral Domain Optical Coherence Tomography (OCT) Images", Proc. SPIE, vol. 7171, 2009, pp. 71710X-1-71710X-8.

Mishra et al., "Intra-Retinal Layer Segmentation in Optical Coherence Tomography Images", Optics Express, vol. 17, No. 26, 2009, pp. 23719-23728.

Mujat et al., "Retinal Nerve Fiber Layer Thickness Map Determined from Optical Coherence Tomography Images", Optics Express, vol. 13, No. 23, 2005, pp. 9480-9491.

Quellec et al., "Three-Dimensional Analysis of Retinal Layer Texture: Identification of Fluid-Filled Regions in SD-OCT of the Macula", IEEE Trans Med Imaging, vol. 29, No. 6, 2010, pp. 1321-1330.

Samarawickrama et al., "Influence of OCT Signal Strength on Macular, Optic Nerve Head, and Retinal Nerve Fiber Layer Parameters", Investigative Ophthalmology & Visual Science, vol. 51, No. 9, Sep. 2010, pp. 4471-4475.

Shahidi et al., "Quantitative Thickness Measurement of Retinal Layers Imaged by Optical Coherence Tomography", American Journal of Ophthalmology, vol. 139, No. 6, Jun. 2005, pp. 1056-1061.

Stein et al., "A New Quality Assessment Parameter for Optical Coherence Tomography", Br J Ophthalmol, vol. 90, 2006, pp. 186-190.

Tan et al., "Mapping of Macular Substructures with Optical Coherence Tomography for Glaucoma Diagnosis", Ophthalmology, vol. 115, 2008, pp. 949-956.

Wu et al., "Factors Associated with Variability in Retinal Nerve Fiber Layer Thickness Measurements Obtained by Optical Coherence Tomography", Ophthalmology, vol. 114, 2007, pp. 1505-1512.

\* cited by examiner (a)

(b)

701

EVALUATION OF OPTICAL COHERENCE TOMOGRAPHIC DATA PRIOR TO SEGMENTATION

CROSS-REFERENCE TO RELATED APPLICATIONS

This application claims priority under 35 USC §119 from provisional application Ser. No. 61/871,467 filed Aug. 29, 2013, the disclosure of which is herein incorporated in its entirety.

TECHNICAL FIELD

This application describes methods to pre-preprocess data obtained from optical coherence tomography systems, in which the quality and usefulness of the obtained dataset are evaluated prior to being subjected to either pre-processing steps such as noise reduction and image enhancement and/or to being subjected to algorithmic analyses such as segmentation.

BACKGROUND

Optical Coherence Tomography (OCT) is a technique for performing high-resolution cross-sectional imaging that can provide images of tissue structure on the micron scale in situ and in real time (see for example Huang et al. "Optical Coherence Tomography" Science 254 (5035): 1178 1991). OCT is a method of interferometry that determines the scattering profile of a sample along the OCT beam. Each scattering profile in the depth direction (z) is called an axial scan, or A-scan. Cross-sectional images (B-scans), and by extension 3D volumes, are built up from many A-scans, with the OCT beam moved to a set of transverse (x and y) locations on the sample. One of the principle advantages of OCT is its ability to image the various layers of the retina of the eye. Technical improvements in this modality permit data sets to be obtained in very short times. Due to these high data rates, it behooves the computational power to keep up with the demands of the instrument and of the clinician or physician, who expect polished images or diagnostic metrics to be displayed instantaneously.

One of the important aspects of clinical diagnoses is that of the retinal nerve fiber layer (RNFL). This is the top layer of the retina seen in OCT imaging of the posterior segment of the eye. Embedded within the retina are the axons of the ganglion cells, residing in the layer just below the RNFL. These axons carry the visual signals (action potentials) to the lateral geniculate nucleus and thus the visual cortex. Impairment of either the ganglion cells themselves or their axons in the RNFL results in a diminution of sight, as would be the case with glaucoma, for example. It has been determined that the earliest observable defect as a result of glaucoma is the thinning of the RNFL (see for example Tan et al. 2008). Early detection is imperative if subsequent treatments are to possess any effectiveness.

A vital diagnostic in the ability to discern the presence or progression of glaucoma, is the thickness of the RNFL. A thinner than expected RNFL suggests the presence of disease. Discovery of thinned RNFLs can be accomplished via visual inspection of each and every OCT A-scan in an OCT dataset, which is naturally time consuming. (An OCT dataset is hereinafter defined to be an array of data from an OCT interferometer in any dimensional form. An image can be the same as or a modified version of a subset of a dataset.)

A substantially more effective approach is via automatic computational segmentation and analysis of the layer: with each slice, edges are detected and distances between these edges or boundaries can be measured. Similar types of analyses can be applied to the edges of the various retinal layers including but not limited to the internal limiting membrane (ILM), ganglion cell layer (GCL), inner plexiform layer (IPL), inner nuclear layer (INL), outer plexiform layer (OPL), and the outer nuclear layer (ONL), external limiting membrane (ELM), and those layers therein below. A discussion of segmentation techniques may be found in US2008100612 (hereby incorporated by reference).

Other retinal characteristics where segmented OCT data can provide useful information include epiretinal membranes, retinal cysts, central serous retinopathy, macular lesions, drusen, macular degeneration, edema, and lesions, subretinal fluid, and intraretinal exudate (Coats' Disease) among others. In the case of subretinal fluid, it is associated with choroidal neovascularization and RPE elevation, which can and will upset the usefulness of many segmentation algorithms.

Segmentation Algorithms

With OCT B-scans, the various retinal depths (layers) in a slice are imaged. It is then imperative to have the ability to segregate the various layers of the retina in an automatic fashion and derive thickness measurements for at least the more vital layers. In order to perform this task, innumerable algorithms have been developed to segment the observations into layers. Clinical evaluation of areas such as the macula and the optic nerve head are likewise vital for similar as well as other reasons. Obviously, it is imperative that the results presented via these automated algorithmic approaches be reliable. Part of the ability in producing reliable results from segmentation algorithms, is the quality of the data input to the algorithm. Besides just plain low signal-to-noise of the data, other possible deficiencies affecting downstream ability to segment layers (hereinafter termed 'segmentability') include poor contact between layers, speckle noise, high-photon absorptivity from hemoglobin (thus creating signal-less shadows), low resolution data (thus blurring the boundaries between layers), eye motion, and saccades, to mention a few. Boundaries are normally found by threshold methodologies which in turn are dependent upon relative reflectances of the layers.

There are a multitude of algorithms to deal with the segmentation problem (see, e.g., DeBuc 2011 and the citations contained therein). Many of these algorithmic approaches deal with either the intensity data or a gradient image and usually assume some basic shape or characteristic. Early attempts used a one-dimensional convolution kernel. More exotic approaches involve optimal graph search methods, Markov random fields, pliable geometric models, graph partitioning, support vector machine (SVM), model-based guidance, neural networks, clustering algorithms (e.g., k-clustering), etc. A common approach has been edge-based detection, and in many cases using a version of the Canny edge-detection methodology. Others have used region-based constraints, which look for similar intensities within a region. Most of these algorithms require considerable computational resources.

Pre-Processing Strategies

Prior to analyses of images by segmentation algorithms, the images are usually pre-processed to improve the sensitivity of the detection algorithm used (e.g., edge or region) to the morphological characteristics of the region of interest. Most of these involve smoothing by various kernels or averaging and speckle noise reduction processing. Typical pre-processing steps could include median filtering: Herzog et al. (2004); mean filtering: Ishikawa (2005); nonlinear anisotropic filtering: Mujat et al. (2005); combination: Baroni et al. (2007); Low/High Pass filtering: Farsiu et al. (2008); wavelets: Quellec et al. (2010); and, fixed-pattern noise removal: Gotzinger et al. (2008). These processing techniques and others would be readily recognized by the ordinary skilled person the art as reducing the contribution of noise to the signal.

Assessing Data Quality

Many of these aforementioned pre-processing strategies will work at least moderately successfully if the data in a dataset are of a high quality: meaning, high signal-to noise-ratio (SNR), and no unexpected gross abnormalities, etc.

A measure of the quality of an image, independent of its morphological characteristics would provide an important metric to avoid analyzing poor data. The independence of the image quality metric from morphology is important otherwise a bias could be introduced as those images tagged as having a low value may be such due to intrinsic, disease-related deficiencies. In other words, diseased retinas could yield low quality metrics.

Several studies have reported on different morphological dependent metrics for evaluating the quality of OCT data including SS (signal-strength), SNR, analysis confidence, and signal deviation (see, e.g., Stein et al. 2005, Wu et al. 2007, and Liu et al. 2009).

SUMMARY

The present application concerns a method of a pre-preprocessing phase of an OCT volumetric or B-scan dataset. This phase segregates good from poor data, based upon a level of the contrast of detected features. It is to be used to identify or eliminate low-quality data which will improve the accuracy of segmentation procedures, hence a more reliable diagnosis of disease potential can be derived.

Additional applications are presented for the basic use of segmentability. It can be used as a real-time measure of focus of the OCT instrument, thus reliable autofocus without operator intervention becomes possible. Another application is in the ability to separate, in real-time operation, a real image from its complex conjugate reflection.

DETAILED DESCRIPTION

Figure 1:
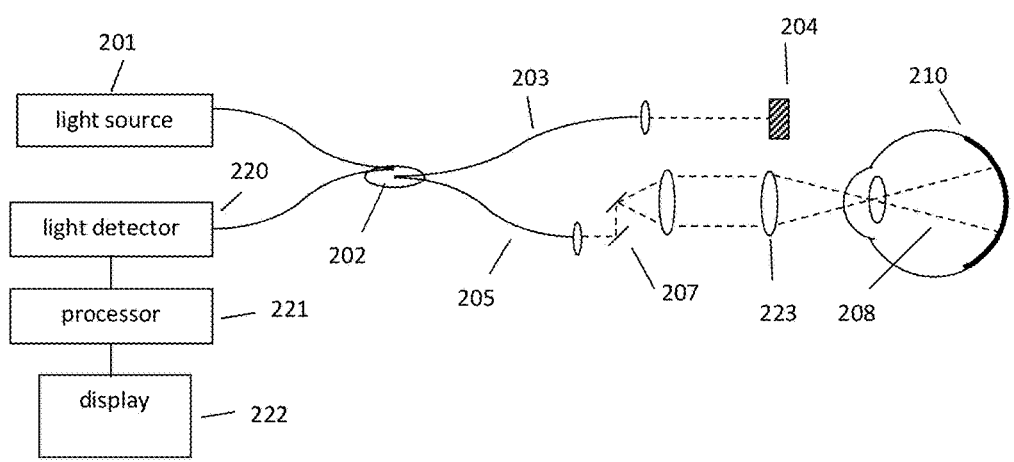
FIG. 1 is a schematic of an FD-OCT system that can be used to collect data for segmentability analysis according to the present invention.

A generalized Fourier Domain optical coherence tomography (FD-OCT) system used to collect an OCT dataset suitable for use with the present set of embodiments, disclosed herein, is illustrated in FIG. 1. A FD-OCT system includes a light source, 201, typical sources including but not limited to broadband light sources with short temporal coherence lengths or swept laser sources.

Light from source 201 is routed, typically by optical fiber 205, to illuminate the sample 210, a typical sample being tissues at the back of the human eye. The light is scanned, typically with a scanner 207 between the output of the fiber and the sample, so that the beam of light (dashed line 208) is scanned over the area or volume to be imaged. Light scattered from the sample is collected, typically into the same fiber 205 used to route the light for illumination. Reference light derived from the same source 201 travels a separate path, in this case involving fiber 203 and retro-reflector 204. Those skilled in the art recognize that a transmissive reference path can also be used. Collected sample light is combined with reference light, typically in a fiber coupler 202, to form light interference in a detector 220. The output from the detector is supplied to a processor 221. The results can be stored in the processor or displayed on display 222. The processing and storing functions may be localized within the OCT instrument or functions may be performed on an external processing unit to which the collected data is transferred. The processing unit can be separated into multiple processors wherein one or more of the processors can be remote from the OCT instrument. The processing unit could be dedicated to data processing or perform other tasks which are quite general and not dedicated to the OCT device. The display can also provide a user interface for the instrument operator to control the collection and analysis of the data. The interface could contain knobs, buttons, sliders, touch screen elements or other data input devices as would be well known to someone skilled in the art.

The interference causes the intensity of the interfered light to vary across the spectrum. The Fourier transform of the interference light reveals the profile of scattering intensities at different path lengths, and therefore scattering as a function of depth (z-direction) in the sample.

The profile of scattering as a function of depth is called an axial scan (A-scan). A dataset of A-scans measured at neighboring locations in the sample produces a cross-sectional image (slice, tomogram, or B-scan) of the sample. A collection of B-scans collected at different transverse locations on the sample comprises a 3D volumetric dataset. Typically a B-scan is collected along a straight line but B-scans generated from scans of other geometries including circular and spiral patterns are also possible.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are typically used at the detection port for SD-OCT systems. The embodiments described herein could be applied to any type of OCT system. The disclosed method relates to processing of an OCT dataset that can be done on the OCT instrument itself or on a separate computer or workstation to which a collected OCT dataset is transferred either manually or over a networked connection.

Embodiments of the present application are designed to analyze an OCT dataset to generate images, metrics, or statistics of an OCT dataset quality, not necessarily correlated directly to signal-to-noise ratio of the data contained therein or to its intensity, but to the contrast found between various structures. The level of the contrast is important in the ability to separate various detected features found in an OCT dataset. A reduction in contrast could be due to, for example, a poorly aligned or defocused OCT instrument. Thus such a metric is usable as a guide for focusing the apparatus. The disclosed method is applicable to volumetric data (3D) or to B-scans (2D) or to A-scans (1D). The approaches of the disclosed method are designed to be fast, and yield real-time or at least near-real-time results for each B-scan (dimensions: z=axial, x=transverse/B-scan, y=perpendicular to B-scan slice). The end-result of this pre-preprocessing step is a metric of data quality, but not one directly related to signal-to-noise ratio or to the intensity of the data, but rather one related to level of the contrast of the OCT signal detections of the various tissues (i.e., retinal layers). The ability to segment the various tissues/retinal layers (segmentability) is dependent upon the level of contrast between the tissues.

Another embodiment of this metric, detailed herein below, is that the segmentability can be the sum of the values in a computed gradient image in the axial direction. Thus segmentability will produce a low value of the metric for an OCT signal with high intensity pixel or voxel values but a low level of contrast: meaning, in a practical sense, blurred edges or poor layer separation. Thus the metric could also be used as a guide for OCT focusing and one that distinguishes between a true image and its complex conjugate. (The complex conjugate image of an OCT image has the same energy as the true OCT image but with lower level of contrast as compared with that of the true OCT image.)

The metric derived from this algorithm is a measure of feature strength in the OCT dataset. (A feature is defined by its edges and intersection of its edge lines in an OCT dataset.) This can be distinguished from the signal strength and SNR. The signal strength and SNR are global and statistical metrics whereas the segmentability is calculated from the local contrast. For example, a blurry image can have high signal strength with low segmentability due to poor contrast. In any of the various definitions of a 'metric' given hereinabove, a map of its values can be displayed to the user.

A pre-segmentation algorithm that signals bad or even poor data, such as the one described in the present application, would be a valuable feature to reduce the chances that such deficient data has been included in segmentation analysis, thus leading to erroneous results, not necessarily recognizable by the clinician.

The disclosed method has been intentionally designed to be simple and fast. There are few parameters to optimize or choose, it uses linear filtering, and real-time implementation is possible. Thus automatic acceptance/rejection of B-scans during acquisition is possible. Furthermore, segmentability of outer/inner retina divided by the defined centroid or a layer is likely with no additional computation expenditure. Another usage of this algorithm is to aid the segmentation and localization of the optic nerve head (ON H) in an OCT-enface image/dataset due to the fact that the ONH region shows a low level of contrast which leads to poor segmentability.

In one embodiment of the present application suitable to a volumetric (3D) dataset, the approach first involves defining a 2D surface from within a 3D volume dataset of OCT data. From this initial 2D surface, based upon either signal features or pre-determined values in the orthogonal dimension, the 2D surface is expanded into a 3D sub-volume. Further manipulation of the data of this volume yields statistics and metrics which then can be used to decide if the data themselves (pixel or voxel values) are of sufficient quality for segmentation algorithms to produce a reliable result.

In this embodiment specific to volumetric (3D) data, a 2D surface is computed based upon selecting a representative value for the location of a certain signal feature in A-scan data. Such signal features could correspond to the ILM or to the RPE or other desired detected features. The collective ensemble of these z-positions then defines a 2D surface. From the latter, a z-interval is applied to each determined location or centroid in the z-dimension to inflate this 2D surface into a 3D volume, which is then a sub-dataset of the original 3D volume of an OCT dataset.

If the dataset is from a B-scan, then a curve is derived from the 2D dataset. A 2D area can be defined by inflating the curve in the orthogonal dimension by pre-determined amounts or from positions of detected features. This 2D sub-dataset is further processed into a map, or metrics, or statistics which can then be displayed and inspected by a clinician or automatically assessed to determine whether the scan meets a certain criterion for the level of contrast so as to decide to perform further processing or a new scan.

In the case of a B-scan (2D dataset), a 1D curve is computed based upon similar criteria as given in the previous paragraph. In this embodiment, the collective ensemble of z-positions then defines this 1D curve. From the latter, a z-interval is applied to each determined location or centroid to inflate the curve into a 2D area, which is a sub-dataset of the original B-scan dataset. The basic method of the present application will be outlined herein below, applicable to any of the embodiments described herein of determining the segmentability on an OCT full 3D dataset or the embodiment of processing a B-scan (meaning the volume contains only a 2D surface, a single B-scan, and is filled only in x and z, and y can be considered to be fixed).

Figure 2:
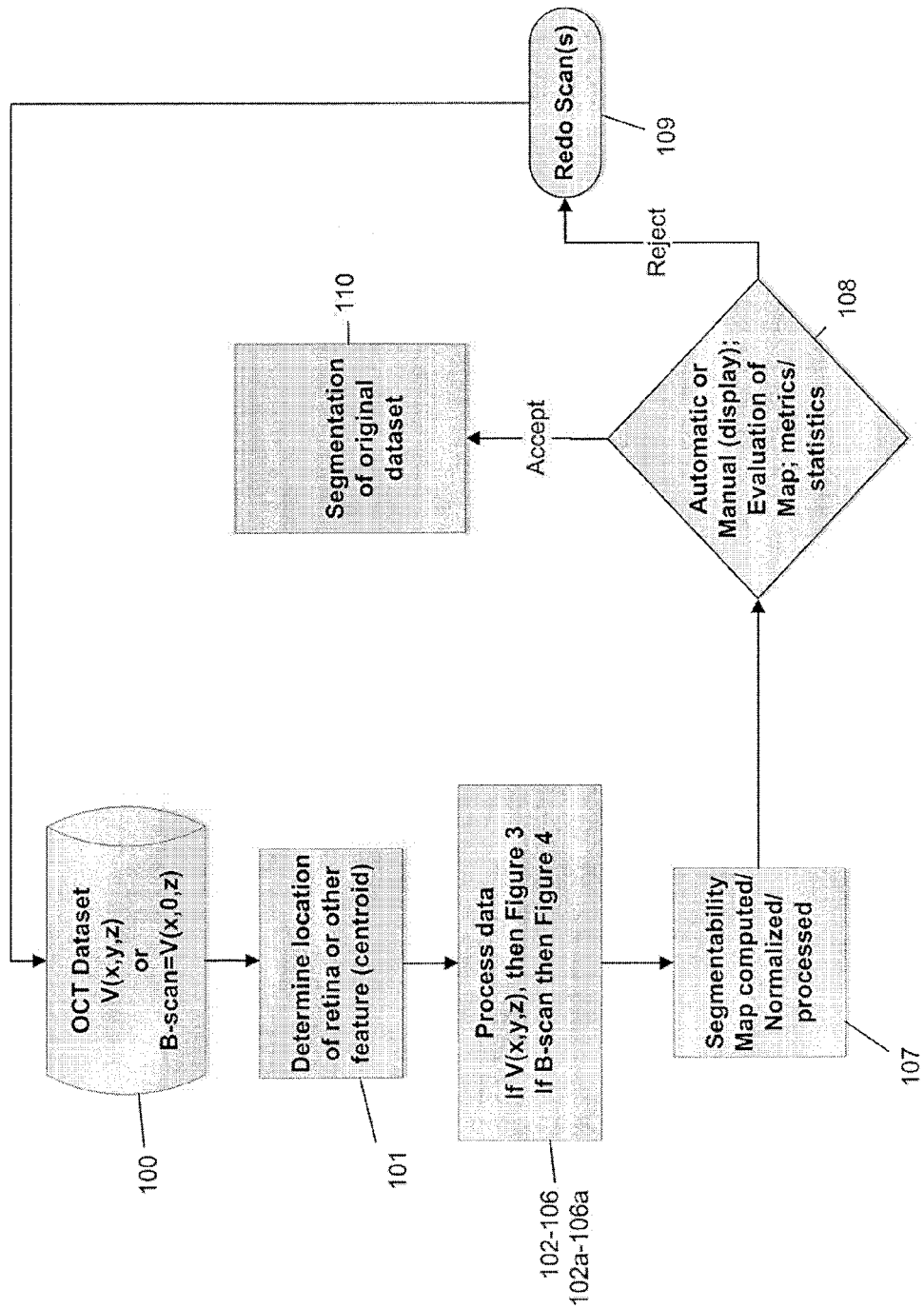
FIG. 2 is a flow chart that summarizes the basic steps of one embodiment of the segmentability determination applicable to an OCT dataset.
Figure 3:
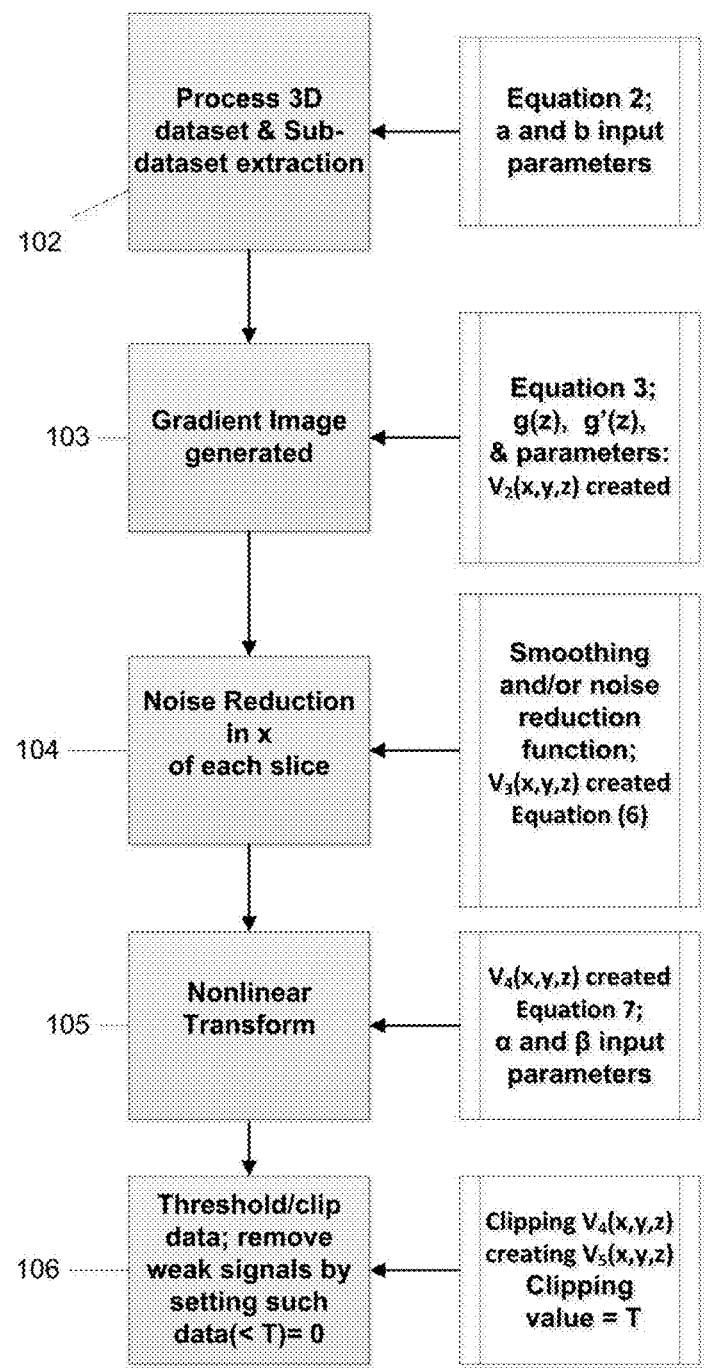
FIG. 3 is a flow chart that summarizes the principal data processing steps of the segmentability method given in FIG. 2 for 3D volumetric OCT dataset.
Figure 4:
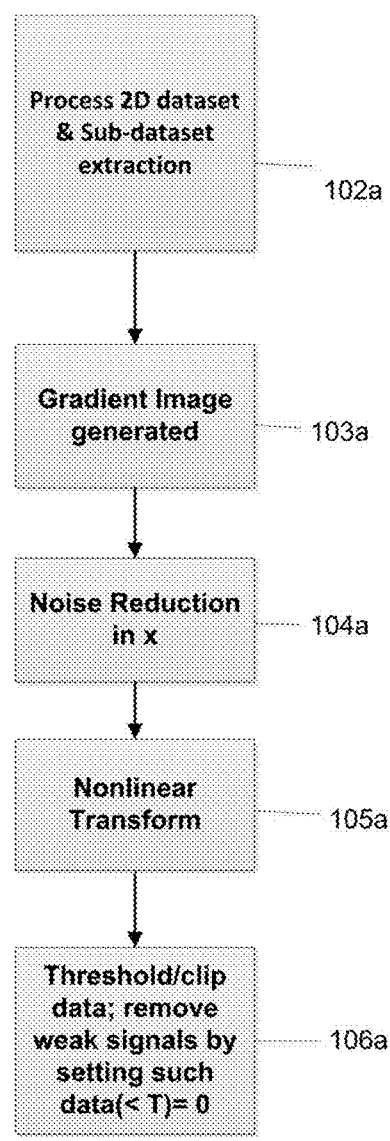
FIG. 4 is a flow chart that represents the principal data processing steps of the segmentability method given in FIG. 2 for B-scan (slice or 2D surface) dataset.

The flow charts of FIGS. 2, 3, and 4 present the overall method to obtain a map or metrics or statistics that can be used to distinguish low contrast data from that of high contrast data. The analysis can be carried out by a processor 221 (or processors) that is part of the OCT dataset collection system or to which a collected OCT dataset is transferred either via network or temporary storage device. FIG. 2 presents the overall method, applicable to either 3D or 2D datasets, with FIG. 3 dealing with the specific processing of a 3D dataset, and FIG. 4 associated with the same steps as FIG. 3 but for a 2D (B-scan) dataset.

In the case of a B-scan, there is the understanding that the y variable is fixed or can be ignored, thus defining a 2D dataset within a 3D dataset.

Referring to FIG. 2, let V(x,y,z) be an OCT dataset 100. In the first step 101 of the method, a feature or representative value of the dataset is identified. If z is the axial dimension and x/y are the transverse dimensions, then a representative value of the location of the retina in the axial direction can be derived generally from:

$$c(x, y) = \frac{\int f(z)[V(x, y, z) - V_0]dz}{\int V(x, y, z)dz}. \tag{1}$$

For classical centroids, $f(z)=z$ and $V_0=0$. $V_0$ may be a constant in any combination of x,y,z. In this latter case, the centroid is taken as the representative value of the location of the retina or any other desired feature. Any representative value of the location of the retina or any other feature in the A-scan is appropriate, such as: an average of the pre-determined retinal minimum and maximum z-values; any normalized linear combination of these two z-values; convolving the volumetric intensity data with a non-constant, nonlinear functional form; or, convolving with an f(z), but where the intensity of the dataset has had the background level removed. In this last case, a possibility would be to clip the background, and calculate a representative value of the location of the retina on the remaining signal or to binarize it (thresholding the remaining signal, in which signals above a certain threshold are set to a value of one, and anything less than this threshold is set to zero intensity).

Figure 5:
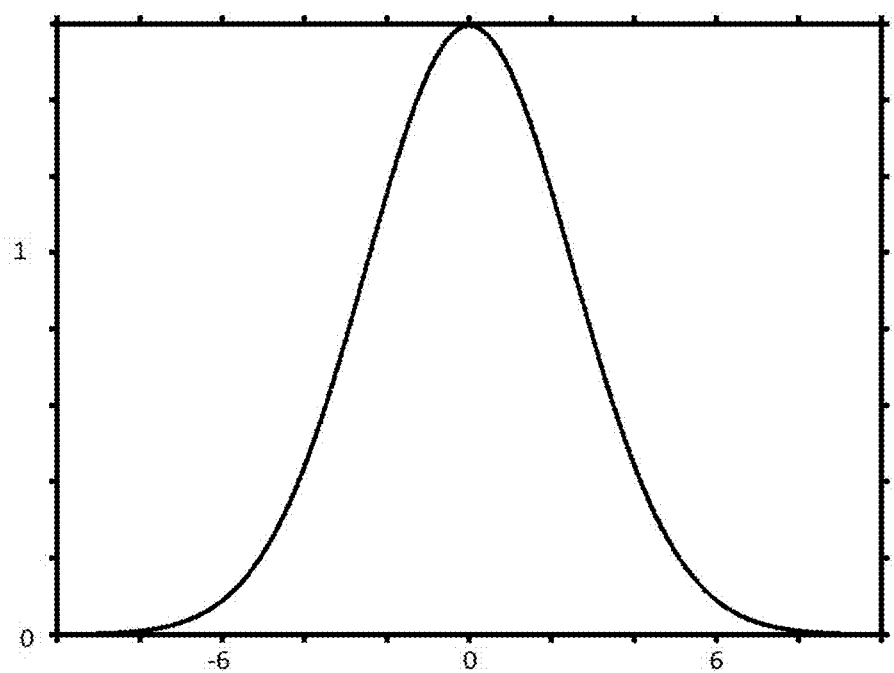
FIG. 5 shows a graphical representation in 5a of the Gaussian derivative function which is convolved with the data only in an A-scan (axial or z-dimension); while 5b is the Gaussian function used in smoothing the x-coordinate of the 2D slice data. (A convolution, well known in the signal processing arts, is defined as multiplying two functions together resulting in a third function.)
Figure 5:
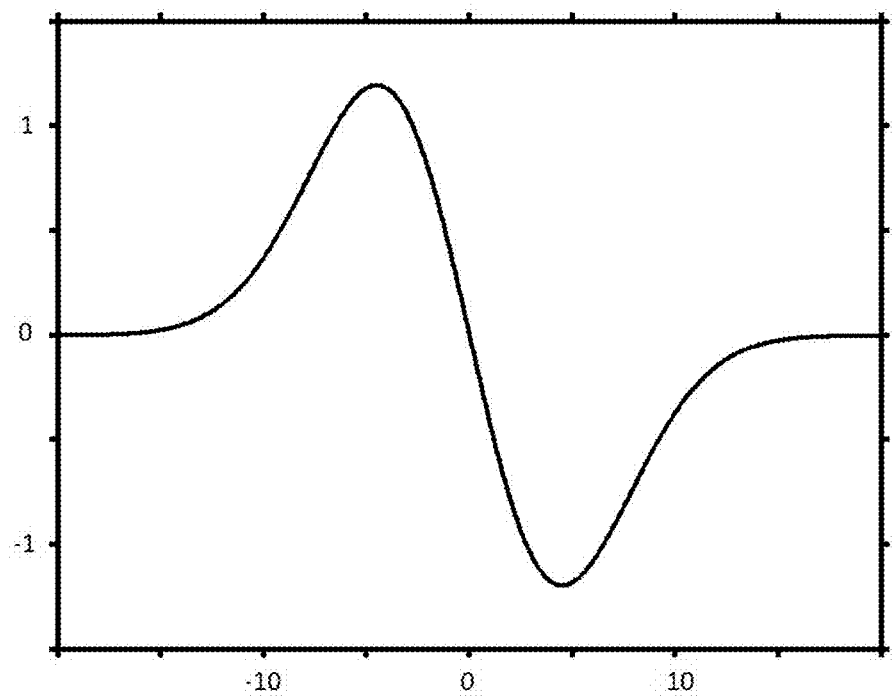

In the next step 102/102a of the method, the representative value can be used to define a sub-dataset within the full dataset. In one embodiment, the centroids or representative values of the location in the A-scan 101 of some anatomical feature can be used to define a surface (for 3D dataset—FIG. 3) or a curve (2D dataset—FIG. 4) within the original full dataset 100. A region of interest about each centroid (along the z-axis) can then be selected, thus selecting a sub-dataset within the full dataset. A sub-dataset $V_1(x,y,z)$ can be extracted from V(x,y,z) within a range along the axial direction (z) as follows:

$$V_1(x,y,z)=V(x,y,z_1)$$

$$z_1 \in [\min(c(x,y))-a\max(c(x,y))+b] \tag{2}$$

Where a and b are constants or offsets from the minimum and maximum value of centroid c(x,y), or the representative value of the location of some anatomical feature. The values of a and b can be estimated from the approximate retinal thickness from an ensemble of OCT datasets, from some pre-determined values, or from detected features found within the signal. The next step 103/103a in the method is to create a gradient image along each A-scan by convolving each z-segment of $V_1(x,y,z)$ with a function. The gradient image represents the directional change in the intensity in an image. In this embodiment, the directional change in axial direction is calculated, although in another embodiment presented hereinbelow this technique is generalized to two directions. The absolute value of the gradient image is taken as a local indicator of the local image contrast. The integral of the gradients in the axial direction for a given A-scan indicates the overall contrast of that A-scan. Higher local contrast leads to better segmentation in general. In this particular embodiment, the derivative of a Gaussian function is used as depicted in FIG. 5a. The advantage of the use of the gradient image is that it is not dependent upon local absolute intensity values. The created gradient image dataset, $V_2(x,y,z)$, can be represented by:

$$V_2(x, y, z) = \int_{-\infty}^{+\infty} g'(z-\tau)V_1(x, y, \tau)d\tau. \tag{3}$$

If g(z) is the Gaussian function $$g(z) = \frac{1}{\sigma\sqrt{2\pi}} e^{-\frac{z^2}{2\sigma^2}} \tag{4}$$

then g'(z) is its derivative:

$$g'(z) = -\frac{z}{\sigma^2}g(z) \tag{5}$$

The next step 104/104a is to smooth or reduce the noise in the x-dimension (along a slice), at each fixed y-value for each slice (meaning for each value of y and each value of z) according to:

$$V_3(x, y, z) = \int_{-\infty}^{+\infty} g(x-\tau)V_2(\tau, y, z)d\tau, \tag{6}$$

where g(x) is the same functional form as g(z) just with x substituted for z and with the same or different standard deviation (as depicted in FIG. 5b). Optional smoothing techniques involve standard median or mean filtering.

Low-pass filtering done in the frequency domain is likewise applicable to this step.

Besides the use of a derivative Gaussian function, optional functions that could be convolved 103/103a with the intensity data in the axial dimension to create a gradient image are Prewitt or Sobel operators, Laplacian, Kirsch compass, Marr-Hildreth, difference of Gaussians, Laplacian of Gaussians, higher-order Gaussian derivatives, Roberts cross, Scharr operator, Ricker wavelet, Frei-Chen or any discrete differentiation operator well known to the ordinary skilled person in the art.

Figure 6:
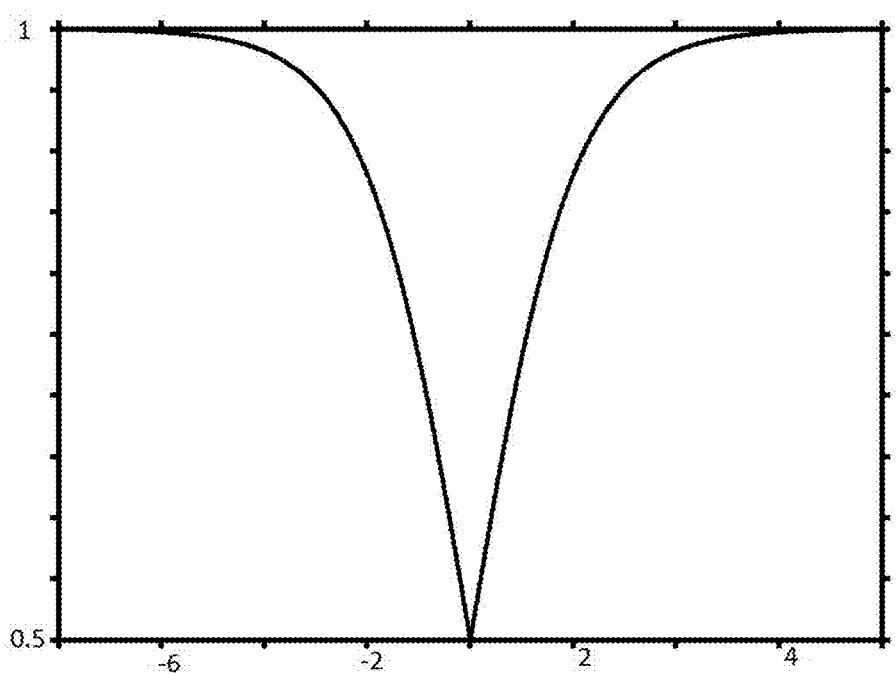
FIG. 6 presents the graphical representation of the sigmoid function used in the derivation of the segmentability map or metric. This particular function is symmetric about zero, as the absolute value of the exponent is taken.

Additional approaches can use multi-scale techniques such as Log-Gabor wavelets and phase congruency (Kovesi 2003) to generate gradient images and extract image features as well. Phase congruency is highly localized and invariant to image contrast which leads to reliable image feature detection under varying contrast and scale. The method of phase congruency applies to features with small derivative or smooth step where other methods have failed. The next step 105/105a in the algorithm is to apply a nonlinear transform function to each absolute value of $V_3(x,y,z)$. The nonlinear transformation is the symmetrized sigmoid function:

$$V_4(x, y, z) = \frac{1}{\left(e^{\frac{-(|V_3(x,y,z)|-\beta)}{\alpha}} + 1\right)}, \quad (7)$$

where $\alpha$ and $\beta$ are sigmoid function parameters. This function is depicted in FIG. 6.

The resultant dataset is then subjected to a clipping (or threshold) value=T 106/106a: meaning only pixels that exceed T are counted in the result.

$$V_5(x,y,z) = \lfloor V_4(x,y,z) - T \rfloor \quad (8).$$

The symbol $\lfloor \ \rfloor$ denotes that the enclosed quantity is equal to itself when its value is positive, and zero otherwise 106/106a. This step eliminates noise as well as facilitating faster processing of the remaining data. An optional approach is to threshold the individual A-scans comprising each B-scan. The next step 107 in the algorithm is to generate a 2D dataset from the volumetric dataset or a 1D dataset (curve) from the B-scan dataset by integrating $V_5(x,y,z)$ from the previous step in the z-axis (axial or depth) direction as follows:

$$S(x,y) = \int V_5(x,y,z)dz \quad (9) \text{ (for volumetric 3D data)}$$

$$S(x) = \int V_5(x,0,z)dz \quad (10) \text{ (for B-scan/2D data)}$$

In the case of the B-scan, the variable y in Equation 10, is naturally ignored or can be considered to be a constant. $S(x,y)$ or $S(x)$ is the segmentability map which can be scaled between a range of zero and one. This map represents the local segmentability quality of an OCT dataset. Moreover, this map can be input to other algorithms to derive additional metrics or to identify a region of interest on a retina such as the optic nerve head (e.g., FIG. 7, 701). At this point the surface $S(x,y)$ or $S(x)$ can be normalized 107 to facilitate display or further processing.

Figure 7:
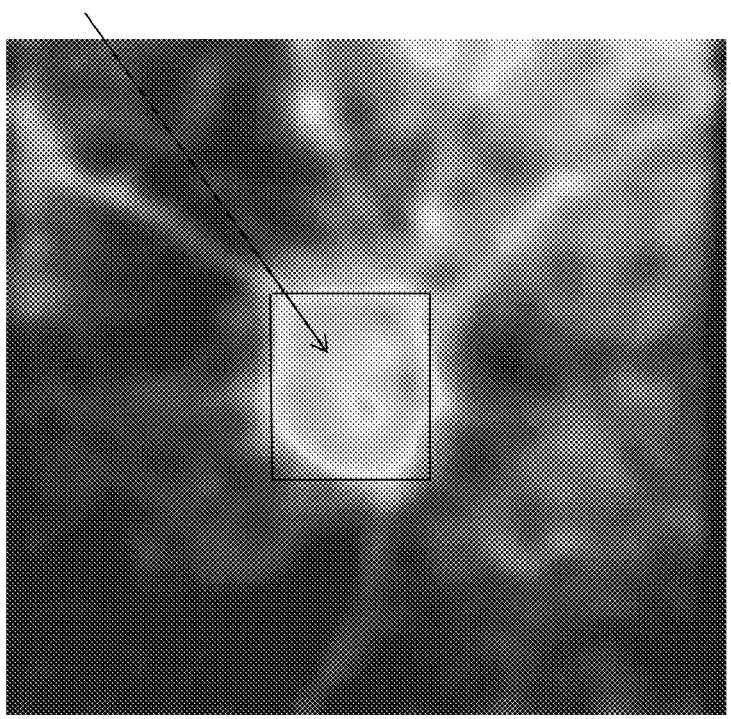
FIG. 7 is an image of a segmentability map and is the result of a volume scan (6×6×2 mm$^3$) about the optic nerve head (ONH, 701). The map can be used to detect the location of the ONH and to segment its boundary. The marked rectangular region is that of the ONH, which has no detected structure, as would be expected. Thus this area cannot be segmented by any algorithm, as there is nothing to segment (no ILM nor RPE etc.)
Figure 7:
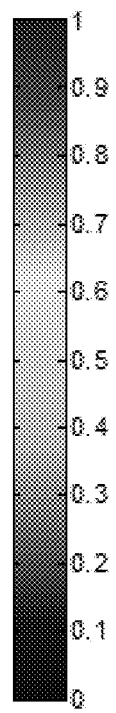
Figure 8:
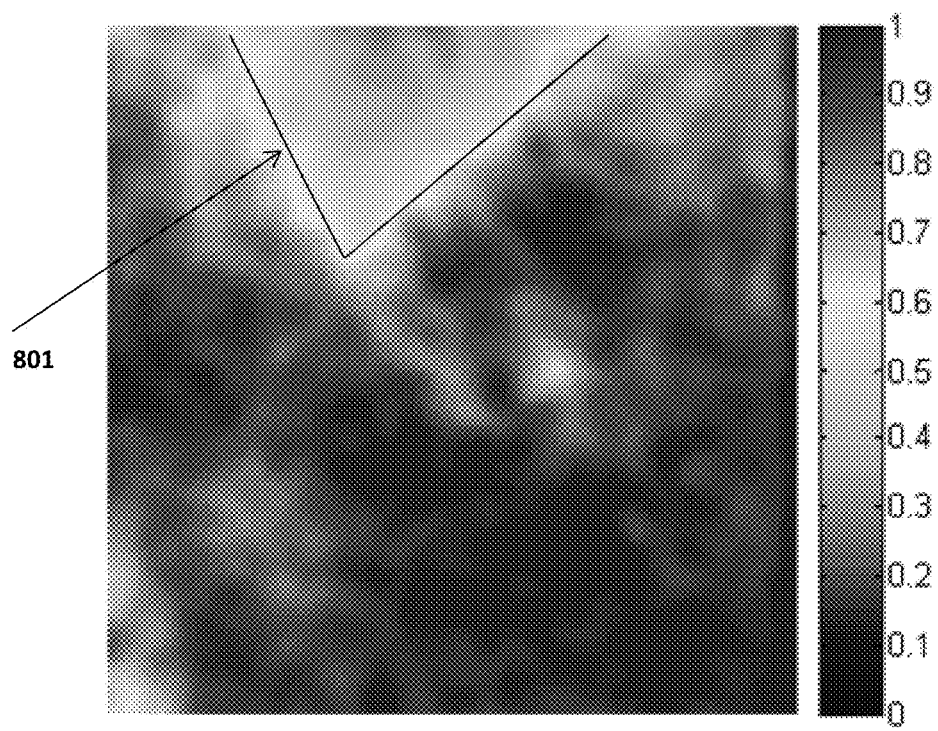
FIG. 8 is an image of a segmentability map and covers a volume of 6×6×2 mm$^3$ centered on the macula. Two lines (801) are shown that demarcate the approximate lower edges of the quasi-triangular region that cannot be segmented due to poor data quality in that particular area. The scans would have to be repeated.

FIGS. 7 and 8 are segmentability maps that have been generated based on the integration of $V_5$ along the axial direction and represent the local segmentability quality of an OCT volume based on the contrast or level of the contrast of the data. FIG. 7 is the result of applying the process described above to a volume scan containing the optic nerve head (ONH, 701). This map can be used to detect the location and to segment the boundary of the ONH. FIG. 8 is the result of a volume around the macula. Both FIGS. 7 and 8 are from scans of a volume 6×6×2 mm². These figures were generated using a classical centroid of the A-scans and the z-interval about the determined centroid was chosen to be approximately the limiting ILM and the RPE z-positions. FIG. 8 shows an area that cannot be segmented. It is outlined by the two oblique lines 801.

Figure 9:
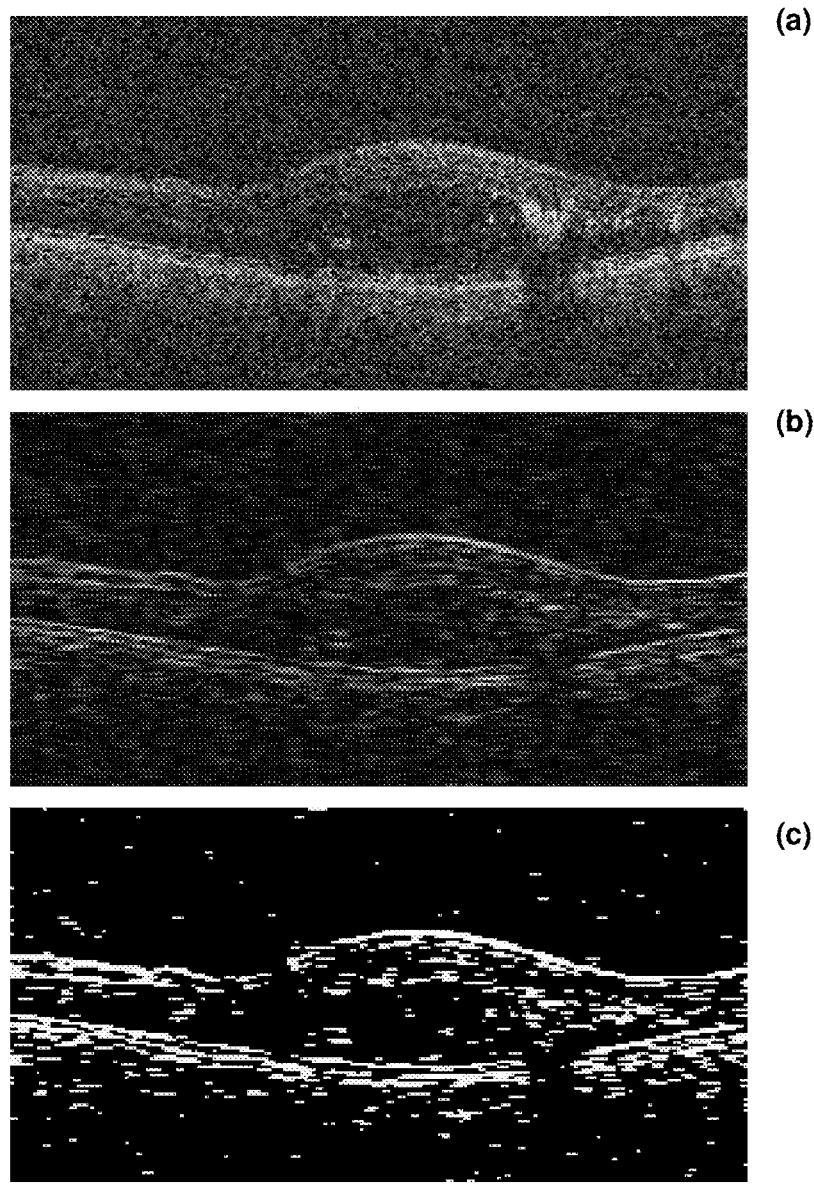
FIG. 9a is an image from a raw-intensity dataset; 9b is the gradient image of the image of 9a, and 9c is the image derived after setting a threshold value on the image data represented by 9b.

A sequence of images as shown in FIG. 9 demonstrates the sequence of steps in the method for a single B-scan: FIG. 9a is a slice of intensity data, FIG. 9b is the convolution of these data with g'(z) and g'(x), and FIG. 9c is the threshold image, a slice of $V_5(x,y,z)$.

The segmentability map $S(x,y)$ can be displayed (108 on a display 222) to the clinician for review on a user interface and the clinician or instrument operator can indicate acceptance or rejection when optionally prompted for a response.

An alternative is to have an automatic rejection or acceptance of the map. The display can be in a full-frame window, or in a sub-window of the corresponding B-scan (the x and z dimensions displayed). If the data are rejected either manually or automatically, the scan or scans can be redone 109. In the case of acceptance 110, the original dataset $V(x,y,z)$ then can undergo pre-processing as outlined in the Background section of the present application, and/or then further analysis via segmentation algorithms.

Image quality statistics can be determined and provided to the clinician on the display 222 from analysis of the aforementioned metrics, e.g., percentage of A-scans above a certain threshold or location of deficient A-scans to identify potentially diseased areas. Weighting the above-threshold number of A-scans, or similarly the below-threshold number of A-scans, with distance from some physical location, such as the fovea or the optical nerve head (ONH) could serve as a useful diagnostic statistic.

The segmentability map can be analyzed 108 to derive metrics and statistics (which could be displayed to a user), including but not limited to:

1) extracting spatial information such as ONH or regions with low segmentability by applying a threshold the values contained within the map;

2) statistical analyses such as moments as classification features could help classify the map which results in acceptance or rejection of the scanned volume;

3) the map could be divided into various sub-maps, or centric subfields, which contains the mean or median segmentability value which then could be display or communicated to the clinician to accept/reject the scan;

4) further analyses of the map could provide simple instructions to the user on potential changes in scan setup that could result in a better image.

A Focus Metric

Figure 10:
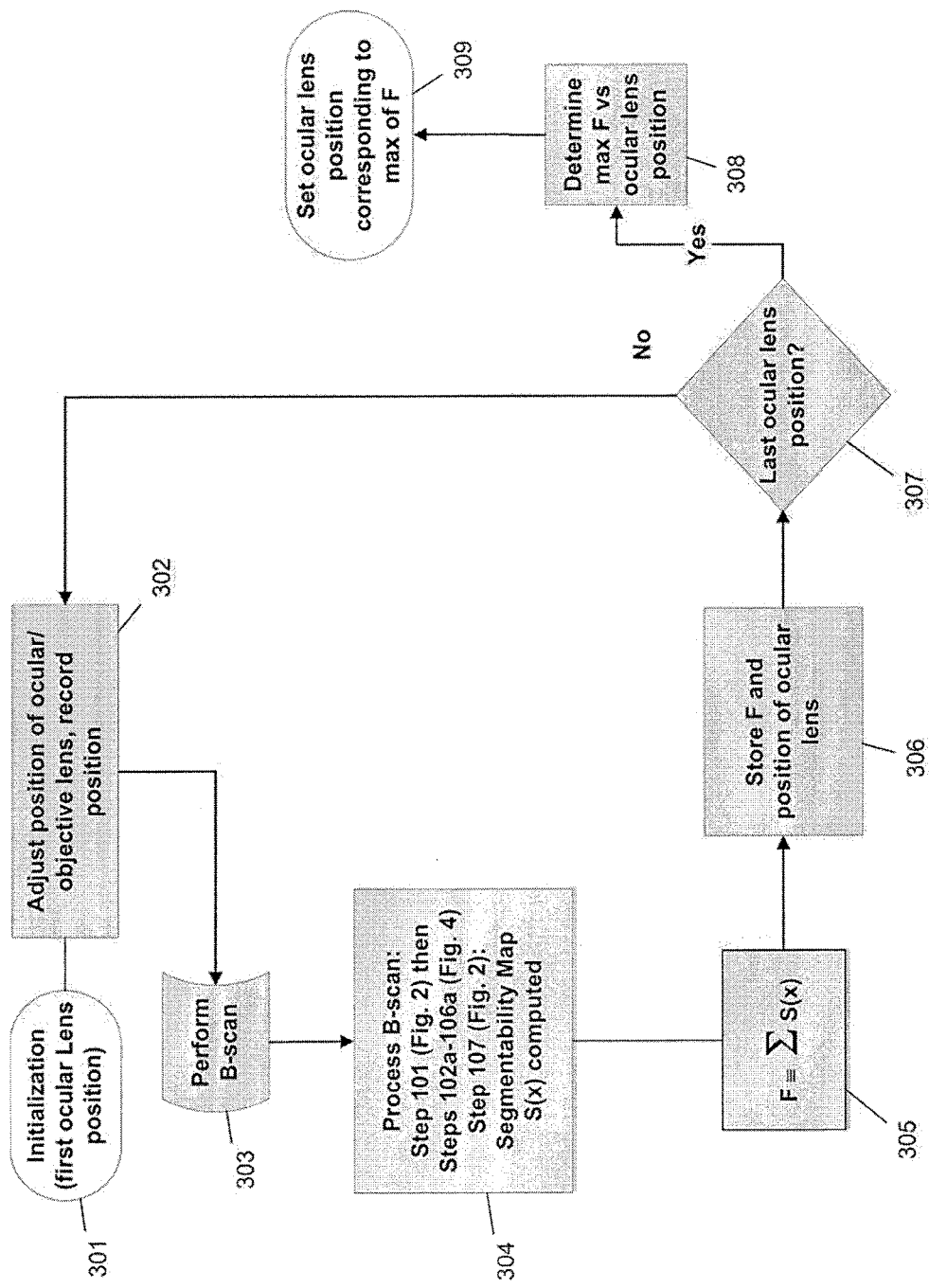
FIG. 10 illustrates the process steps to determine optimum focus of the OCT instrument.

Segmentability can be used as a metric correlated to the focus quality of the optical coherence tomography (OCT) instrument. In FIG. 10, the basic steps to achieve the best focus are outlined. The OCT system is first initialized (step 301) with control over the position of the ocular/objective lens 302 within the instrument. An acquisition/-processing loop is then entered (either by manual action or via an automatic procedure) which takes a B-scan 303 dataset at each position of the ocular lens, processes the dataset (first step will be that of 101 in FIG. 1, then the steps 102a to 106a according to the flow chart in FIG. 4) to compute a segmentability map 304, sums the segmentability map over S(x) 305 with the summed value=F, stores the position of the ocular lens 223 and F 306, performs a check to see if the lens has reached the end of its longitudinal travel 307, and if not repeats the steps. Once the entire sequence of steps has been performed, the maximum value F is found and its associated value of the position of the ocular lens is determined (308), and the lens position can be set accordingly (309).

Distinguishing Real and Complex Conjugate Images

A deficiency in the use of Fourier-domain OCT, is that its practical use is limited by the complex conjugate ambiguity, which is inherent to real Fourier transforms. Due to this artifact, an FD-OCT image or dataset obtained from a real-valued spectral interferogram will consist of two overlapped images symmetrical with respect to the zero phase delay of the interferometer. Thus, only one half of the imaging depth range is useful in practice. Resolving the complex conjugate ambiguity would double the imaging depth range and provide additional flexibility by allowing arbitrary positioning of the zero plane, e.g., moving it inside the sample. It is well known that the complex conjugate image is of low quality, meaning that the level of contrast between its layers or features is substantially lower than the contrast between those equivalent layers found in the real image.

Figure 11:
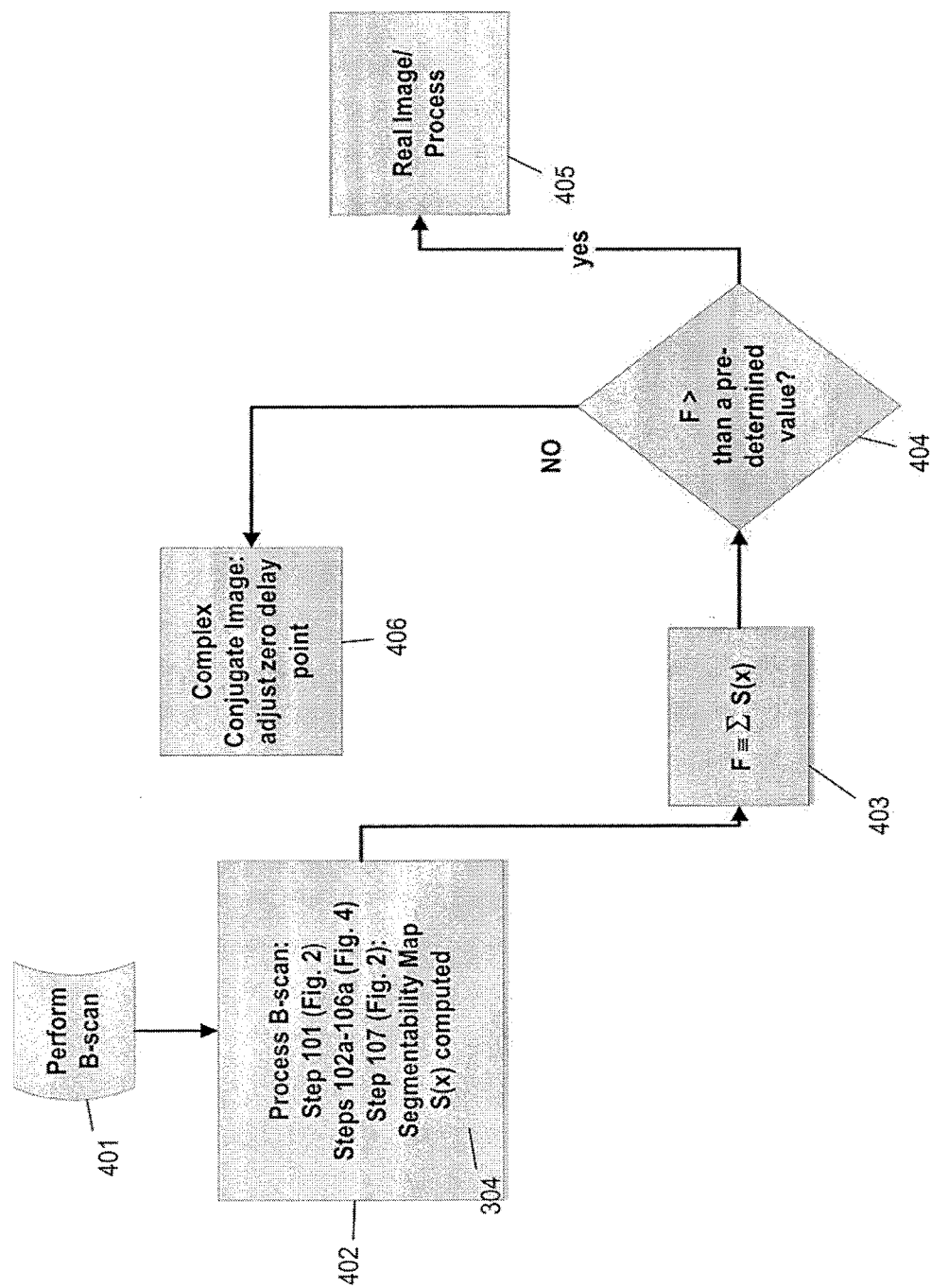
FIG. 11 illustrates the process steps to determine if the detected image is real or the complex conjugate.

Thus a measure of the of the level of the contrast via a segmentability map is applicable to distinguish the real image from that of the complex conjugate image. FIG. 11 is a flow chart of the basic procedure for this purpose.

A B-scan is performed 401, and the obtained dataset is processed 402 as indicated by step 101 (FIG. 1) and then steps 102a-106a (FIG. 4). The segmentability map is then summed (=F) as in the case of the focus procedure described in FIG. 10 403. If the value of F is greater than a threshold value 404, the latter of which can be pre-determined from previous analyses, then the image is the real one and leads to further analyses 405 as described in this application. If the value of F is less than the threshold value, then the complex conjugate image has been identified and the appropriate reconfiguration of the instrument can occur 406, which is normally an adjustment of the zero delay point, and then the scan is repeated 401.

Another embodiment of the present application is a methodology to automatically classify the metric or metrics of segmentability into sharp vs blurred categories. There is also a third possibility—neither; in other words, noise or background, possessing little signal.

The axial scan (either gradient or intensity) is divided into portions or segments, as a function of the z-dimension. For each of these portions, one or more metrics, as described previously, are computed. From the ensemble of metrics obtained from a collection of A-scans, an unsupervised classifier is used to segregate the metrics into different types or levels and as a function of the axial dimension. For a sharp structure in the A-scan, e.g. a real image, a metric would possess a value distinct from that of one which was derived from a more blurred structure found in a different part of that A-scan (i.e., complex conjugate image). Noise or background would possess a third characteristic, one which is referred to here as 'neither.'

In the case of focus, however, blurring an image by defocus would affect both real and complex conjugate images. The metrics derived from real and complex conjugate images respectively would approach each other in value. If the blurring was sufficiently strong, then the respective metrics would nearly be the same. Thus by comparing the statistics of the metrics, the blurring effects of focus can be separated from the blurred images of the complex conjugate.

Once these metrics have been classified, additional processing of the results can occur, such as taking a ratio of the mean value of one isolated distribution (or clustering of values) to that of another, or by partitioning of the data into Dirichlet tessellations (see, e.g., Okabe et al. 2000), or by providing a weighted composite metric. This will help identify more clearly the relative contrast of the various signals derived from the A-scan. By identification of which portion of the A-scan (or A-scans) correspond to the complex-conjugate image, then the zero delay position can be altered and the data re-acquired.

There are two types of learning that are commonly used in statistical analyses: supervised and unsupervised. From a theoretical point of view, supervised and unsupervised learning differ only in the causal structure of the model. In supervised learning, the model defines the effect of one set of observations, called inputs, has on another set of observations, called outputs. In other words, the inputs are assumed to be at the beginning and outputs at the end of the causal chain. The models can include mediating variables between the inputs and outputs.

In unsupervised learning, all the observations are assumed to be caused by latent variables, that is, the observations are assumed to be at the end of the causal chain. In practice, models for supervised learning often leave the probability for inputs undefined. This model is not needed as long as the inputs are available, but if some of the input values are missing, it is not possible to infer anything about the outputs. If the inputs are also modelled, then missing inputs cause no problem since they can be considered latent variables as in unsupervised learning.

The goal of unsupervised learning is to build representations of the input data that can be used for decision making. It can be thought of as finding patterns in the input data above and beyond that which would be considered pure unstructured noise. Two examples of unsupervised learning are clustering and dimensional reduction. Moreover, almost all work in unsupervised learning can be viewed in terms of learning a probabilistic model of the data. Thus such a probabilistic model can be used for classification. (For an introduction to statistical learning techniques, please see, Hastie et al. 2009.)

Once the data have been collected and the measured metrics segregated by the unsupervised classifier, then additional collection of data to establish the relationship between metrics of sharp images, those of blurred image, and those which are neither, will be less important.

In an embodiment, the unsupervised classifier may automatically organize the A-scans or metrics derived therefrom on the basis of at least one clustering algorithm. The unsupervised classifier may automatically organize the A-scans or metrics derived from each A-scan or subimages thereof on the basis of at least one of the following: self-organizing map of neural computing, t-distributed stochastic neighbor embedding, principal component analysis, sammon mapping method, GTM (General Topographic Mapping), LLE (Locally Linear Embedding) mapping, Isomap, agglomerative or hierarchial hierarchal clustering, including single-link-, complete-link-, average-link clustering, clustering error minimization, distance error minimization, K-means clustering, K-method, and graph-based methods like single- or complete link clustering, density based method, density-based spatial cluster of applications with noise (DBSCAN), AUTOCLASS, SNOB, BIRCH, MCLUST, or model based clustering COBWEB or CLASSIT, simulated annealing for clustering, genetic algorithms, Bayesian method, Kernel method, Multidimensional scaling, principal curve, T-SNE, some of their combination or the like. (For an introduction to these and other clustering algorithms, please see Duda et al. 2001.)

In supervised learning, the statistical classifier could be any of the following, or even any combination of the following: artificial neural network, Bayesian statistics, Hopfield networks, Boltzmann machines, decision trees, inductive logic programming, random Forests, ordinal classification, regression analysis, fuzzy networks or clustering, conditional Random Field, support vector machine, multilayer perception network, principal component analysis, hybrid realization, and symbolic machine learning. In addition, the person having ordinary skill in the art would readily recognize alternatives to these listed algorithms, as well as those alternatives for the unsupervised classifying algorithms.

Upon automatic organization of the metrics, A-scans, or their subimages, by the unsupervised classifier, and the various distributions identified, a classification score can be assigned. This score represents a distribution of input values. The classification scores will be related to the level of contrast, which might be caused as focused, unfocused, real, or complex conjugate images, noise (or none-of-the-above), or any combination of these characteristics. In the simplest case, these scores would be sharp, blurred, and neither. The score can be interpreted as a probability and as such the sum total of scores should be one.

An additional embodiment would be defining a metric based upon a measure of the breadth of the autocorrelation function. Examples would be its standard deviation, a measure of its width (e.g., FWHM), or any measure of the sharpness of the autocorrelation function.

Although various applications and embodiments that incorporate the teachings of the present method have been shown and described in detail herein, those skilled in the art can readily devise other varied embodiments that still incorporate these teachings.

REFERENCES: (HEREBY INCORPORATED BY REFERENCE)

Patent Literature

US2008100612
U.S. Pat. No. 7,575,322
U.S. Pat. No. 7,330,270
US2012249956

Non-Patent Literature

Tan et al. (2008), 'Mapping of Macular Substructures with Optical Coherence Tomography for Glaucoma Diagnosis,' Ophthalmology 115, 949-956.
Canny (1986), 'A computational Approach to Edge Detection,' IEEE Trans. Pattern Anal. Mach. Intell., PAMI-8(6), 679-698.
Wu et al. (2007), Factors associated with variability in retinal nerve fiber layer thickness measurements obtained by optical coherence tomography, Ophth 114, 1505-1512.
Liu, S. et al. (2009), 'Quality assessment for spectral domain optical coherence tomography (OCT) Images,' Multimodal Biomedical Imaging IV, Proc. SPIE 7171.
Stein et al. (2006), 'A new quality assessment parameter for optical coherence tomography,' Brit. J. Ophthal., 90, 186-190.
DuBuc D. C. (2011), 'A Review of Algorithms for Segmentation of Retinal Image Data Using Optical Coherence Tomography,' Chap. 2, in *Image Segmentation*, Ed. P.-G. Ho, Pub: InTech, 15-54.
Kovesi (2003), Phase Congruency Detects Corners and Edges. In: The Australian Pattern Recognition Society, Proc. DICTA, 309-318.
Herzog et al. (2004), 'Robust Extraction of the Optic Nerve Head in Optical Coherence Tomography,' CVAMIA-MM-BIA, LNCS 3117, 395-407.
Ishikawa et al. (2005), 'Macular Segmentation with Optical Coherence Tomography,' Inv., Ophth. Vis. Sci., 46(6), 2012-2017.
Mujat et al. (2005), Retinal nerve fiber layer thickness map determined from optical coherence tomography images. Optics Exp 13(23), 9480-9491.
Baroni et al. (2007), 'Towards quantitative analysis of retinal features in optical coherence tomography,' Medical Engineering and Physics 29(4), 432-441.
Farsiu et al. (2008), 'Fast detection and segmentation of drusen in retinal optical coherence tomography images,' Photonics West, Ophthalmic Technologies. San Jose, Calif.; 68440D-68441-68412.
Quellec et al. (2010), 'Three-dimensional analysis of retinal layer texture: identification of fluid-filled regions in SD-OCT of the macula,' IEEE Trans. Med. Imaging 29(6), 1321-1330.
Götzinger et al. (2008), 'Retinal pigment epithelium segmentation by polarization sensitive optical coherence tomography,' Opt. Exp 16(21), 16410-16422.
Okabe et al. (2000), *Spatial Tessellations*, Wiley, ISBN 9780471986355.
Duda et al. 2001, *Unsupervised Learning and Clustering*, Wiley, ISBN 0471056693.
Hastie et al. 2009, *The Elements of Statistical Learning*, Springer, ISBN 978038794857.

It is claimed that:

1. A an optical coherence tomography (OCT) system comprising:
a light source for generating a beam of light;
a splitting element for splitting the beam of light into reference and sample arms;
optics for scanning the beam over the eye to generate a data set including a plurality of A-scans, each A-scan defining a scattering profile as a function of depth;
a detector for receiving interfering light from the sample and reference arms and generating signals in response thereto;
a display; and
a processor for converting the signals into the dataset and identifying a feature of interest within the data set, said processor determining the level of contrast in a portion of the dataset that includes the feature, said level of contrast corresponding to the integral of the intensity gradients extending along an A-scan within the feature, said processor determining the segmentability of the processed portion of the dataset based on the determined level of contrast corresponding to the integral of the intensity gradients and wherein the processor causes the results of the determination or a further analysis thereof to be stored or displayed on the display.

2. The system as recited in claim 1, in which the OCT dataset is either two-dimensional or three-dimensional.

3. The system as recited in claim 1, in which the entire dataset is processed.

4. The system as recited in claim 1 wherein the processor generates a segmentability map of the dataset based on the determined segmentability.

5. The system as recited in claim 4, in which the segmentability map is displayed, stored, or further processed.

6. The system as recited in claim 1, further comprising re-acquiring OCT data based on the results of the determination.

7. The system as recited in claim 1, wherein the processor generates one or more metrics that reflect the level of the contrast in the data and wherein the determined metrics are stored or displayed.

8. The system as recited in claim 1, in which the feature of interest is a surface or curve within the OCT dataset and the level of contrast is determined by processing a portion of the dataset containing said surface or curve with a function and storing the portion of the processed dataset as a second dataset.

9. The system as recited in claim 8, in which the surface or curve is derived from a representative value of the location of a region of interest from A-scans.

10. The system as recited in claim 8, in which the function is selected from the group consisting of Gaussian derivative, higher-order Gaussian derivatives, Laplacian, Kirsch compass, difference of Gaussians, Laplacian of Gaussian, vertical Prewitt operator, Marr-Hildreth, vertical Sobel operator, Roberts cross, Frei-Chen, Ricker Wavelet, and Scharr operator.

11. The system as recited in claim 8, in which the second dataset is further processed with a second function in a spatial dimension.

12. The system as recited in claim 11, in which the said second function is selected from the group consisting of Gaussian, mean filtering, median filtering, and low-pass filtering in the frequency domain.

13. The system as recited in claim 8, in which the data of one or more A-scans or one or more B-scans from said OCT dataset are subjected to a threshold function.

14. The system as recited in claim 13, in which statistics are extracted from each scan and said statistics are displayed, stored or further processed.

15. The system as recited in claim 14, in which said statistics are weighted by their distance from a reference point from within the second dataset.

16. The system as recited in claim 14, in which one or more metrics are derived from said statistics.

17. The system as recited in claim 16, in which said reference point is the fovea or the optical nerve head.

18. The system as recited in claim 17, in which the one or more metrics are derived from the group consisting of moment analysis, threshold analysis, median, mode, and mean segmentability values.

19. The system as recited in claim 18, in which each scan is weighted by the one or more metrics.

20. The system as recited in claim 19, wherein the OCT system includes an autofocus mechanism and wherein the one or more metrics are used to control autofocus mechanism.

* * * * *

UNITED STATES PATENT AND TRADEMARK OFFICE
CERTIFICATE OF CORRECTION

PATENT NO. : 9,778,021 B2  
APPLICATION NO. : 14/466774  
DATED : October 3, 2017  
INVENTOR(S) : Homayoun Bagherinia It is certified that error appears in the above-identified patent and that said Letters Patent is hereby corrected as shown below:

In the Specification

In Column 6, Line 23, delete "(ON H)" and insert -- (ONH) --, therefor.

In Column 11, Line 5, after "measure" delete "of the".

In Column 12, Line 39, delete "hierarchial hierarchal" and insert -- hierarchical --, therefor.

In the Claims

In Column 14, Line 17, in Claim 1, delete "A an" and insert -- An --, therefor.

Signed and Sealed this  
Twenty-sixth Day of June, 2018

Andrei Iancu  
*Director of the United States Patent and Trademark Office*